(12) United States Patent
Lim et al.

(10) Patent No.: US 11,331,263 B2
(45) Date of Patent: May 17, 2022

(54) MALE CLEANSER AND MANUFACTURING METHOD THEREOF

(71) Applicant: ANDIVA INC., Chuncheon-si (KR)

(72) Inventors: Young Chul Lim, Chuncheon-si (KR); Jung Ho Ahn, Chuncheon-si (KR)

(73) Assignee: ANDIVA INC., Chuncheon-si (KR)

( * ) Notice: Subject to any disclaimer, the term of this patent is extended or adjusted under 35 U.S.C. 154(b) by 200 days.

(21) Appl. No.: 16/782,603

(22) Filed: Feb. 5, 2020

(65) Prior Publication Data

US 2020/0206127 A1 Jul. 2, 2020

Related U.S. Application Data

(63) Continuation of application No. PCT/KR2019/009491, filed on Jul. 30, 2019.

(30) Foreign Application Priority Data

Aug. 2, 2018 (KR) .................. 10-2018-0090392
Dec. 14, 2018 (KR) .................. 10-2018-0162275

(51) Int. Cl.
*A61Q 19/10* (2006.01)
*A61K 8/9789* (2017.01)
(Continued)

(52) U.S. Cl.
CPC ............... *A61K 8/9789* (2017.08); *A61K 8/20* (2013.01); *A61K 8/34* (2013.01); *A61K 8/345* (2013.01);
(Continued)

(58) Field of Classification Search
CPC .......... A61Q 19/10; A61K 8/345; A61K 8/34; A61K 8/416; A61K 8/365; A61K 8/9794
(Continued)

(56) References Cited

U.S. PATENT DOCUMENTS

2006/0018867 A1* 1/2006 Kawasaki ............ C08G 77/452
424/70.122
2009/0214628 A1* 8/2009 de Rijk .................. A61P 17/02
424/450

(Continued)

FOREIGN PATENT DOCUMENTS

KR 20060128964 12/2006
KR 101319990 10/2013
(Continued)

OTHER PUBLICATIONS

Andiva TIESO for man SET male cleansing & soothing cream, https://smartstore.naver.com/andiva/products/2988731095?NaPm=ct%3Dk1uiiuj4%7 Cci%3Dbf3ff6318bdb82a0b1ae7cb93bdcf9ac8147c7f0%7Ctr%3Dimg%7Csn%3D720677%7Chk%3Dd41e312f14894639e05127f36f5d01cba98967be, Naver Shopping: Dr. Andiva.

(Continued)

*Primary Examiner* — Eisa B Elhilo
(74) *Attorney, Agent, or Firm* — Cantor Colburn LLP

(57) ABSTRACT

Provided is a male cleanser including a skin conditioner, a solvent, a humectant, a viscosity increasing agent, a surfactant, a preservative, a chelating agent, and perfume, wherein the skin conditioner includes a Maca root extract, a natural extract, niacinamide, glyceryl acrylate/acrylic acid copolymer, hyaluronic acid, arginine, hydrolyzed collagen, sucrose distearate, hydrogenated lecithin, and dimethicone.

14 Claims, 1 Drawing Sheet

(51) Int. Cl.
   *A61K 8/9794*   (2017.01)
   *A61K 8/20*     (2006.01)
   *A61K 8/34*     (2006.01)
   *A61K 8/365*    (2006.01)
   *A61K 8/41*     (2006.01)
   *A61K 8/43*     (2006.01)
   *A61K 8/44*     (2006.01)
   *A61K 8/73*     (2006.01)

(52) U.S. Cl.
   CPC .............. *A61K 8/365* (2013.01); *A61K 8/416* (2013.01); *A61K 8/43* (2013.01); *A61K 8/44* (2013.01); *A61K 8/735* (2013.01); *A61K 8/9794* (2017.08); *A61Q 19/10* (2013.01)

(58) Field of Classification Search
   USPC ....................................................... 424/78.03
   See application file for complete search history.

(56) References Cited

U.S. PATENT DOCUMENTS

2017/0156999 A1* 6/2017 Harris ................... A61K 8/8129
2017/0252388 A1* 9/2017 Baban ................... A23L 33/125

FOREIGN PATENT DOCUMENTS

KR    20160022172    2/2016
KR    20180071558    6/2018

OTHER PUBLICATIONS

International Search Report—PCT/KR2019/009491 dated Oct. 29, 2019.
Pi.Gene Genee Honey for Man, https://blog.naver.com/pi-gene-jey/221318113492, Naver Blog: Pigieneglobervolumetalks.

* cited by examiner

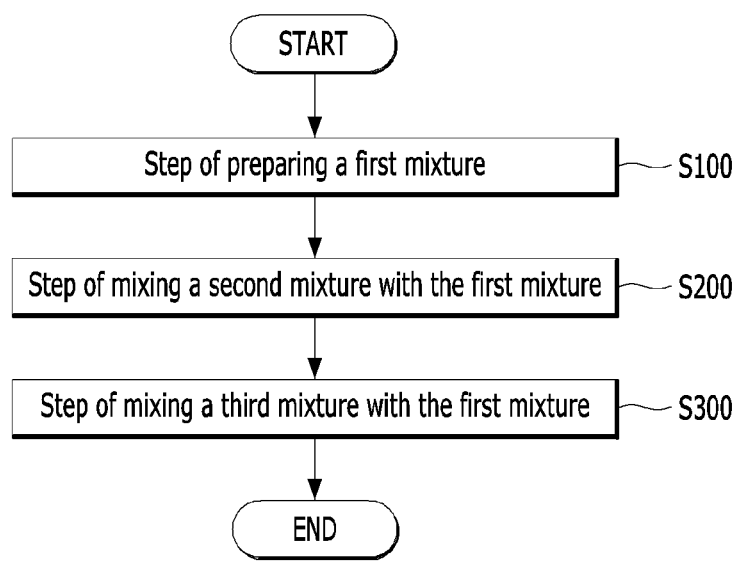

MALE CLEANSER AND MANUFACTURING METHOD THEREOF

TECHNICAL FIELD

The present invention relates to a male cleanser and a manufacturing method thereof.

BACKGROUND ART

Lately, men's interest in the appearance has greatly increased, men's cosmetic products have diversely been developed accordingly, and male consumers' response to the men's cosmetic products is also known to be positive.

Various cosmetic products ranging from basic cosmetic products for skin care to color cosmetic products as men's cosmetic products have been developed. A male cleanser, as in a female cleanser, is a kind of cosmetic products for cleaning genital periphery, armpit or the like. The genital periphery or armpit have a high possibility of giving out a bad odor since the skin of the genital periphery or armpit is folded. Therefore, the genital periphery or armpit needs care. However, the situation is that the cosmetics industry has a very low perception for a male cleanser market, and the number of male cleanser products sold is remarkably lack compared to female cleanser products having similar uses.

On the other hand, Maca has been receiving attention as male health material. Maca, as a brassicaceae plant native to the Andes of South American continent has been noted for containing abundant protein, unsaturated fatty acid, mineral, etc. Particularly, since Maca includes important fatty acids such as linolenic acid, palmitic acid and oleic acid, and an intrinsic unsaturated fatty acid such as macaene or macamide, and is effective in promotion of testosterone secretion, overcoming of menopause obstruction, etc. Therefore, since reproductive ability can be improved when Maca is ingested, or cosmetic products based on Maca are used, a research for developing a composition using Maca has been progressed.

Korean Patent Laid-Open Publication No. 2016-0022172, i.e., a background technique of the present invention, relates to a composition for male health enhancement. The above-mentioned Korean Patent Laid-Open Publication No. 2016-0022172 discloses a composition for male health enhancement including a Maca extract and a food or pharmaceutical composition including the composition, but does not disclose cosmetic products including the Maca extract and effects thereof.

DISCLOSURE

Technical Problem

The present invention is to solve problems of the above-mentioned existing techniques, and an object of the present invention is to provide a male cleanser.

Further, the other objective of the present invention is to provide a method of manufacturing the male cleanser.

However, technical problems to be achieved by embodiments of the present invention are not limited to the above-mentioned technical problems, and another technical problems may exist.

Technical Solution

As a technical means for achieving the above-mentioned technical objects, a first aspect of the present invention provides a male cleanser including a skin conditioner, a solvent, a humectant, a viscosity increasing agent, a surfactant, a pH adjusting agent, a chelating agent, and perfume, wherein the skin conditioner includes a Maca root extract, a natural extract, chlorhexidine digluconate, arginine, menthol, and hyaluronic acid.

According to an embodiment of the present invention, although the male cleanser may include 0.5 to 11 parts by weight of the Maca root extract and 0.1 to 5 parts by weight of the natural extract based on 100 parts by weight of the male cleanser, the present invention is not limited thereto.

According to an embodiment of the present invention, although the natural extract may include a material selected from the group consisting of a Morus alba root extract, a green tea extract, a persimmon leaf extract, an aloe vera leaf extract, a chamomile flower extract, a *Portulaca oleracea* L. extract, and combinations thereof, the present invention is not limited thereto.

According to an embodiment of the present invention, although the skin conditioner may additionally include a material selected from the group consisting of butylene glycol, purified water, 1,2-hexanediol, glycerin, and combinations thereof, the present invention is not limited thereto.

According to an embodiment of the present invention, although the Maca root extract may include a material selected from the group consisting of a Maca powder, a Maca hot water extract, and a combination thereof, the present invention is not limited thereto.

According to an embodiment of the present invention, although the solvent may include purified water, glycerin, ethanol, 1,2-hexanediol and butylene glycol, the present invention is not limited thereto.

According to an embodiment of the present invention, although the humectant may include glycerin, the present invention is not limited thereto.

According to an embodiment of the present invention, although the male cleanser may further include a viscosity increasing agent including a material selected from the group consisting of a xanthan gum, hydroxyethyl cellulose and a combination thereof, and a surfactant including cocamidopropyl betaine, sodium chloride, lauryl hydroxysultaine, decyl glucoside, and octyldodeceth-16, the present invention is not limited thereto.

According to an embodiment of the present invention, although the male cleanser may further include a chelating agent including citric acid and disodium EDTA, the present invention is not limited thereto.

According to an embodiment of the present invention, although the male cleanser may include 0.1 part by weight or less of chlorhexidine digluconate based on 100 parts by weight of the male cleanser, the present invention is not limited thereto.

According to an embodiment of the present invention, although the male cleanser may further include a pH adjusting agent including citric acid, the present invention is not limited thereto.

Furthermore, a second aspect of the present invention provides a method of manufacturing a male cleanser, the method including the steps of: preparing a first mixture including purified water, glycerin, a first surfactant, hyaluronic acid, a viscosity increasing agent, arginine, a chelating agent, and a pH adjusting agent; mixing a second mixture including ethanol, 1,2-hexanediol, a second surfactant, menthol, perfume and chlorhexidine digluconate with the first mixture; and mixing a third mixture including purified water, a Morus alba root extract, a green tea extract, a persimmon leaf extract, an aloe vera leaf extract, a chamomile flower extract, a *Portulaca oleracea* L. extract and butylene glycol with the first mixture.

According to an embodiment of the present invention, although the first surfactant may include purified water, sodium chloride and lauryl hydroxysultaine, and the second surfactant may include octyldodeceth-16, the present invention is not limited thereto.

According to an embodiment of the present invention, although the step of preparing the first mixture may be performed at a temperature of 50° C. to 70° C., the present invention is not limited thereto.

According to an embodiment of the present invention, although the step of preparing the third mixture may include the steps of: preparing a first material by mixing a Maca root extract, butylene glycol, purified water and 1,2-hexanediol; and preparing a second material by mixing purified water, butylene glycol, a Morus alba root extract, a green tea extract, a persimmon leaf extract and an aloe vera leaf extract, the present invention is not limited thereto.

The above-mentioned means for solving problems is only illustrative, and should not be interpreted to be intended to limit the present invention. In addition to the above-mentioned exemplary embodiments, additional embodiments may exist in drawing and the detailed description of the present invention.

Advantageous Effects

According to the above-mentioned means for solving problems of the present invention, a male cleanser according to the present invention is nontoxic and does not have side effects with the human body since the male cleanser includes a natural extract.

Further, the natural extract of a male cleanser according to the present invention includes a Maca root extract, an aloe vera leaf extract, a *Portulaca oleracea* L. extract, a chamomile flower extract, a Morus alba root extract, a green tea extract, and a persimmon leaf extract as active ingredients. Therefore, a male cleanser according to the present invention has advantages that the male cleanser has excellent effects of moisturizing and soothing the skin.

Further, when a male cleanser according to the present invention is applied to male genitalia, it can be confirmed that length of the male genitalia is extended.

However, effects that can be obtained from the present invention are not limited to the above-mentioned effects, and other effects may exist.

DESCRIPTION OF DRAWINGS

FIG. 1 is a flowchart of a method of manufacturing a male cleanser according to an embodiment of the present invention.

BEST MODE

Hereinafter, examples of the present invention will be described in detail with reference to the annexed drawings so that those skilled in the art will easily be able to implement the present invention.

However, the present invention may be implemented in various forms and not limited to the examples described herein. A part having no relationship with the description is omitted to clearly describe the present invention in the drawings, and similar constituent element is indicated by similar reference numeral throughout the present specification.

In the whole present specification, when a part is referred as to be "connected" to the other part, the parts are not only "directly connected" to each other, but also "electrically connected" to each other while interposing another part therebetween.

In the whole present specification, when any member is positioned "on", "over", "above", "beneath", "under", and "below" the other member, this not only includes a case that the any member is brought into contact with the other member, but also includes a case that another member exists between two members.

In the whole present specification, if a prescribed part "includes" a prescribed element, this means that another element can be further included instead of excluding other elements unless any particularly opposite description exists.

When unique manufacture and material allowable errors of numerical values are suggested to mentioned meanings of terms of degrees used in the present invention such as "about", "substantially", etc., the terms of degrees are used as the numerical values or as a meaning near the numerical values, and the terms of degrees are used to prevent that an unscrupulous infringer unfairly uses a disclosure content in which extract or absolute numerical values are mentioned to help understanding of the present invention.

Further, in the whole present specification, "a step doing ~" or "a step of ~" does not mean "a step for ~".

In the whole present specification, a term of "a combination thereof" included in a Markush type expression, which means a mixture or combination of one or more selected from the group consisting of elements described in the Markush type expression, means including one or more selected from the group consisting of the elements.

In the whole present specification, description of "A and/or B" means "A or B", or "A and B".

Hereinafter, a male cleanser according to the present invention and a manufacturing method thereof will be described in specifically with reference to embodiments, examples and drawing. However, the present invention is not limited to such embodiments, examples and drawing.

As a technical means for achieving the above-mentioned technical objects, a first aspect of the present invention provides a male cleanser including a skin conditioner, a solvent, a humectant, a viscosity increasing agent, a surfactant, a pH adjusting agent, a chelating agent, and perfume, wherein the skin conditioner includes a Maca root extract, a natural extract, chlorhexidine digluconate, arginine, menthol, and hyaluronic acid.

Generally, a male cleanser means a cosmetic product for removing odor emitted from genital peripheral skin, armpit or the like and ameliorating the genital peripheral skin or the skin of the armpit. The male cleanser may include a skin conditioner for moisturizing the skin, a solvent for dissolving the skin conditioner, a humectant which is injected into the solvent to maintain moisture of the solvent, a viscosity increasing agent which increases viscosity of the male cleanser such that the male cleanser does not flow down from the skin, a surfactant for mixing of the skin conditioner and the solvent, a pH adjusting agent for adjusting a pH value of the male cleanser such that the male cleanser has a weak acidity or a weak alkalinity, a chelating agent for preventing small amounts of metal ions from flowing in the male cleanser, and perfume for emitting incense.

Although a surfactant according to the present invention may include a cleaning agent for removing contaminants in the male cleanser, a solubilizing agent for transparently dissolving a small amount of oil in the solvent, an emulsifier for allowing the oil and solvent to be mixed well, a foam promoter for increasing efficacy of other surfactant by forming bubbles, etc., the present invention is not limited thereto.

A skin conditioner according to the present invention means a material for skin moisturizing and soothing effects and skin health amelioration. The skin conditioner may include a moisturizer or humectant which allows moisture to be remained on the skin by pulling moisture in the air, an emollient or occlusive which suppresses evaporation of moisture by producing an oil film on the skin, miscellaneous substances for giving special ingredients to the skin, etc.

According to an embodiment of the present invention, although the male cleanser may have a form selected from the group consisting of a gel, a cream, an ointment, a cosmetic water, a pack, and combinations thereof, the present invention is not limited thereto.

According to an embodiment of the present invention, although active ingredients of the male cleanser may be the Maca root extract, the natural extract, the chlorhexidine digluconate, the menthol, the arginine, and the hyaluronic acid, the present invention is not limited thereto.

According to an embodiment of the present invention, although the Maca root extract may include a material selected from the group consisting of a Maca powder, a Maca hot water extract, and a combination thereof, the present invention is not limited thereto.

A Maca root extract according to the present invention means an ingredient extracted from root of Maca (Lepidium meyenii Walp), i.e., a brassicaceae plant. The Maca contains important fatty acids such as linolenic acid, palmitic acid and oleic acid, plant sterol, and mineral in large amounts, and may contain an intrinsic unsaturated fatty acid such as macaene or macamide which are not discovered from other plants. Such ingredients have been reported to have biological activities. Particularly, it has been reported that a glucosinolate content of the Maca reaches 100 times that of other brassicaceae plant, and glucosinolate controls the immune system and acts as an anti-cancer.

The Maca has efficacies of promoting blood circulation and enhancing erection of the penis of male by stimulating artery positioned in the penis of male.

According to an embodiment of the present invention, although the male cleanser may include 0.5 to 10 parts by weight of the Maca root extract and 1 to 5 parts by weight of the natural extract based on 100 parts by weight of the male cleanser, the present invention is not limited thereto.

According to an embodiment of the present invention, although the natural extract may include a material selected from the group consisting of a Morus alba root extract, a green tea extract, a persimmon leaf extract, an aloe vera leaf extract, a chamomile flower extract, a *Portulaca oleracea* L. extract, and combinations thereof, the present invention is not limited thereto.

A Morus alba root extract according to the present invention is extracted from Morus alba root, brightens tone of the skin, and may execute an anti-oxidation activity.

A green tea extract according to the present invention means an ingredient extracted from green tea leaves. The green tea extract may exhibit an anti-oxidation activity, an anti-cancer activity, a blood lipid reduction activity in cardiovascular system, and a blood circulation promoting activity, A persimmon leaf extract according to the present invention means an ingredient extracted from persimmon leaves. The persimmon leaf extract has characteristics of allowing the skin to be elastic and strong and has an effect of protecting scalp and hair since the persimmon leaf extract is rich in vitamin A and vitamin C.

An aloe vera leaf extract according to the present invention means an ingredient extracted from aloe. The aloe vera leaf extract has effects of sterilization, lowering cholesterol level, stabilizing endocrine system, improving appetite, anti-cancer, detoxification, resistance to disease, anti-allergy, antihistamine, skin care, skin soothing, etc.

A chamomile flower extract according to the present invention, as an ingredient extracted from chamomile flower, may be called as a Matricaria flower extract. The chamomile flower may be used in bath, beauty care, fomentation, etc., and has effects in insect-proof, soothing, spasmolysis, pain relieving, diaphoresis, digestion promotion, fatigue recovery, etc.

A *Portulaca oleracea* L. extract according to the present invention means an ingredient extracted from *Portulaca oleracea* L. The *Portulaca oleracea* L. is also called as *portulaca*, and means landward annual weeds which are frientlt grown on the pavement. The *Portulaca oleracea* L. extract contains eicosapentaenoic acid, i.e., a type of omega-3 unsaturated fatty acid, and may provide a moisturizing effect and effects of improving skin resistance to external stimulation or bacteria and soothing the skin.

Hyaluronic acid according to the present invention includes amino acid and uronic acid, and means a polymer compound including N-acetyl glucosamine and glucuronic acid. The hyaluronic acid may carry out collagen synthesis within the skin, wrinkle removal, and antibacterial action.

Arginine according to the present invention, as a type of amino acid, may perform a function of storing moisture in the skin by being involved in activity of collagen.

Chlorhexidine digluconate according to the present invention means salt components of chlorhexidine and gluconic acid, is activated in a neutral or weak acidic pH value, and simultaneously performs a function of giving a help in caring clean and neat skin and a function of preventing decomposition of a composition due to microorganisms by removing external materials, contaminants, etc.

According to an embodiment of the present invention, although the male cleanser may include 0.1 part by weight or less of the chlorhexidine digluconate based on 100 parts by weight of the male cleanser, the present invention is not limited thereto.

Menthol according to the present invention means an ingredient obtained by distilling leaves or stems of Mentha piperascens. The menthol helps circulation action of the skin and may give coolness or a feeling of refreshment to the skin.

According to an embodiment of the present invention, although the skin conditioner may additionally include a material selected from the group consisting of butylene glycol, purified water, 1,2-hexanediol, glycerin, and combinations thereof, the present invention is not limited thereto.

Although butylene glycol, purified water, 1,2-hexanediol and glycerin included in the skin conditioner may be butylene glycol, purified water, 1,2-hexanediol and glycerin which are used together with the surfactant to dissolve active ingredients of the male cleanser, or which are for liquefying the active ingredients to supply the active ingredients to the skin, the present invention is not limited thereto.

According to an embodiment of the present invention, although the purified water may be purified water which is obtained by distilling water or passing the distilled water through an ion exchange resin, the present invention is not limited thereto.

According to an embodiment of the present invention, although the solvent may include purified water, glycerin, ethanol, 1,2-hexanediol and butylene glycol, the present invention is not limited thereto.

According to an embodiment of the present invention, although the humectant may include glycerin, the present invention is not limited thereto.

According to an embodiment of the present invention, although the male cleanser may further include a viscosity increasing agent including a material selected from the group consisting of a xanthan gum, hydroxyethyl cellulose and a combination thereof, and a surfactant including cocamidopropyl betaine, sodium chloride, lauryl hydroxysultaine, decyl glucoside, and octyldodeceth-16, the present invention is not limited thereto.

A xanthan gum according to the present invention means a high molecular weight heteropolysaccharide gum obtained by pure culture and fermentation of carbohydrate by using Xanthomonas campestris. The xanthan gum performs functions of increasing viscosity of the male cleanser, suppressing separation of the components of the male cleanser, and supplying moisture to the skin.

Hydroxyethyl cellulose according to the present invention means a modified cellulose polymer component having a hydroxyethyl branched-chain structure, and is known to be excellent in salt resistance and pH stability.

Cocamidopropyl betaine according to the present invention means an amphoteric surfactant obtained by neutralizing a fatty acid obtained from coconut oil with dimethylaminopropylamine, and may be used as a foam promoter or a viscosity increasing agent.

Sodium chloride according to the present invention which is for increasing viscosity of the surfactant may additionally provide an acidity adjusting function and a preservative function.

Lauryl hydroxysultaine according to the present invention, as an amphoteric surfactant, may additionally perform a function of adjusting viscosity of the male cleanser.

Decyl glucoside according to the present invention, as a component obtained by a condensation reaction of decylalcohol and glucose, is a nonionic vegetable surfactant extracted from corn, coconut, palm kernel oil, etc. The decyl glucoside provides skin moisturization, and may also be used as a skin conditioner since the decyl glucoside hardly has irritation on the skin.

Octyldodeceth-16 according to the present invention is a type of a surfactant, i.e., polyethylene glycol ether of octyldodecanol. The octyldodeceth-16 has excellent dermatotropic properties and may help the skin absorb the active ingredients.

According to an embodiment of the present invention, although the male cleanser may further include a chelating agent including citric acid and disodium EDTA, the present invention is not limited thereto.

Citric acid according to the present invention may be called as acidum citricum, and a natural ingredient discovered in citrus fruits. The citric acid may chelate metals such as a diammonium salt, a potassium salt, a sodium salt, etc., and may also be used as a pH adjusting agent, a skin conditioner, a solvent or the like of the male cleanser.

Disodium EDTA according to the present invention means a component which prevents interion bonding. The disodium EDTA may perform a function of giving a help such that a chelating agent for eluting trace amounts of metal ions within the male cleanser, a preservative, and the active ingredients are absorbed into the skin.

According to an embodiment of the present invention, although the male cleanser may further include menthol as the skin conditioner, the present invention is not limited thereto.

According to an embodiment of the present invention, although the male cleanser may include 0.1 to 2 parts by weight of the menthol based on 100 parts by weight of the male cleanser, the present invention is not limited thereto.

In the above description, one material may not perform one function only. For instance, the disodium EDTA may perform functions of the chelating agent and the preservative, and the citric acid may perform functions of the pH adjusting agent and the chelating agent.

Meanwhile, the male cleanser, without including the above-mentioned materials, may include 5 to 20 wt % of a Maca extract, 10 to 30 wt % of a cleaning agent, 0.1 to 3 wt % of lauryl glucoside, 0.1 to 3 wt % of menthoxypropanediol, 0.01 to 0.5 wt % of a pH adjusting agent, 0.1 to 1 wt % of a disinfectant, emulsifiers including 0.1 to 5 wt % of polyglyceryl-10 stearate, 0.1 to 5 wt % of polyglyceryl-3 methylglucose distearate and 0.1 to 5 wt % of polyglyceryl-3 diisostearate, oils including 0.1 to 5 wt % of isopropyl myristate, 0.1 to 5 wt % of Macadamia oil, 0.1 to 5 wt % of silicone oil and 0.1 to 5 wt % of perfluoropolyether, 0.5 to 10 wt % of a block copolymer represented by the following chemical formula 1, and a balance of water:

[Chemical formula 1]

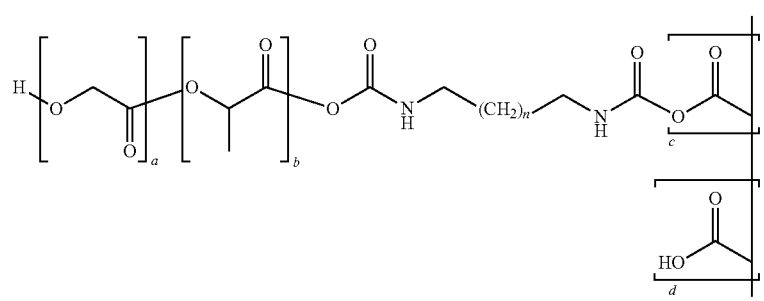

In chemical formula 1, n is a natural number of 2 to 10, and in a to d which show a mole fraction, a is 0.5, b is 0.5, c is 0.05 to 0.2, d is 0.8 to 0.95, and c+d is 1.

Although the male cleanser may include a cleaning agent including sodium lauryl sulfate, cocamidopropyl betaine and disodium cocoamphodiacetate, a disinfectant including ethanol, a disinfection supplement including chloroxylenol, a thickener including guar hydroxypropyltrimonium chloride, and a surfactant including a block copolymer of poly (D,L-lactide-co-glycolide) represented by the chemical formula 1 and polyacrylic acid substituted with a diisocyanate compound, the present invention is not limited thereto.

The block copolymer of poly(D,L-lactide-co-glycolide) and polyacrylic acid substituted with the diisocyanate compound may have a weight average molecular weight range of 10,000 to 100,000, more preferably 30,000 to 70,000. When the block copolymer satisfies the above-mentioned weight average molecular weight range, the copolymer is favorable to the formation of a nanoemulsion.

It is preferable that the copolymer has an average particle diameter range of 10 nanometers to 100 nanometers. When the copolymer has such a particle size range, the copolymer may be excellent in penetration into the skin and collectability of active ingredients. The copolymer obtained as described above may be remarkably stable in an aqueous solution compared with low molecular weight micelles.

In the block copolymer of poly(D,L-lactide-co-glycolide) and polyacrylic acid substituted with the diisocyanate compound, poly(D,L-lactide-co-glycolide) (the following chemical formula 2) and polyacrylic acid substituted with the diisocyanate compound (the following chemical formula 3) may be formed in a bond of an isocyanate group and a hydroxyl group of a carboxyl group.

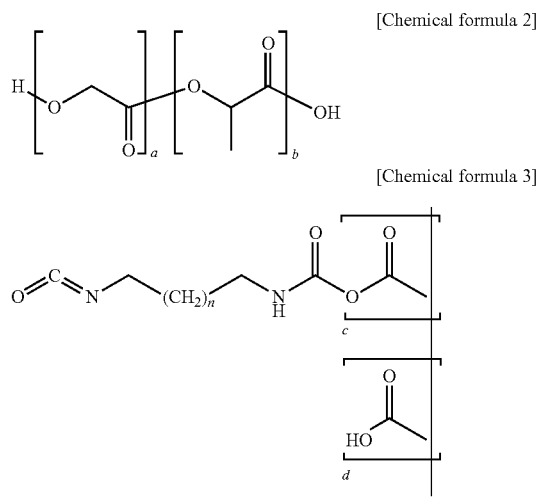

[Chemical formula 2]

[Chemical formula 3]

Further, the male cleanser may further include 3 to 10 wt % of a hot water extract of ingredients including 0.1 to 3 parts by weight of Mastic gum, and 0.1 to 3 parts by weight of a *Boswellia serrata* powder, 0.1 to 3 parts by weight of an erythritol powder, 0.1 to 3 parts by weight of a Sophora tonkinensis Gapnep powder and 0.1 to 3 parts by weight of a Lobelia chinensis powder.

The Mastic (scientific name: Pistacia lentiscus LINNE) is a food additive registered as a natural flavoring substance No. 272 in Korean Food Additives Codex, and Mastic gum is a viscous natural gummi as a sap collected from Anacardiaceae mastic trees which are native to Chios island located in southeastern Greece. An ingredient of mastic has been known to contain 60 to 70% of resin, 33% of αβ-Boswellic acid, 33% of olibanoresene, Arabic acid, etc.

A mastic extract has been known to have anti-inflammatory effect, antioxidant effect and anticancer effect, and has been extensively used in treatment or prevention of inflammatory diseases including arthritis, asthma and inflammatory bowel disease in Korean Medicine. History of Mastic has shown that Ancient Greeks had been known to use Mastic for the purpose of alleviating dysphoria in epigastrium, stomachalgia, dyspepsia and gastric ulcer or use Mastic as an ingredient of a sweetener or beverage, the Arabs have used Mastic oil as food, and Mastic has been known to be frequently used as a beverage or food ingredient even in Iraq. It has been mentioned in "Korean medicine clinical application" of Ahn Deokgyun that, if Mastic prepared in the form of a powder is applied to an affected area when an ulcer is caused by skin infection due to external injury, the Mastic promotes the formation of granulation tissue, removes ache, and is mainly used for the purpose of pain relieving.

The above-mentioned *Boswellia serrata* is native to Africa, Southern Arabia, India, etc., and a green sap is flown out from the cut stem of the *Boswellia serrata* when cutting a stem of the *Boswellia serrata*. A *Boswellia serrata* extract has traditionally been used in inflammation such as a skin rash, an ulcer or the like, or a respiratory disease such as asthma, bronchitis or laryngitis, and has been known to have a medical effect even in arthritis, etc. The *Boswellia serrata* is a typical plant of *Boswellia serrata* genus, and the *Boswellia serrata* extract has been known to exhibit very excellent effects of inhibiting elastase activity and inhibiting decomposition of glycosaminoglycan by containing a large amount of Boswellic acid.

The above-mentioned Sophora tonkinensis Gapnep is a rambling shrub root which is also called as Menispermum dahuricum DC. The above-mentioned Sophora tonkinensis Gapnep has been known to inhabit at sunny hillsides in all parts of Korea and contain alkaloid, dauricine, tetrandrine, and the like in roots and stems thereof (Yakugawa Zasshi 1970). Further, sinomenine and dauricine have been known to have antispasmodic activity and have efficacy even in hypertension and anti-inflammatory action, and an access to a rheumatism therapeutic agent is currently being researched by extracting and fractionating total alkaloids (Acta Med Okayama 1976).

The above-mentioned Lobelia chinensis contains various bioactive substances as a medicinal plant used as a herb medicine in Korean Medicine. The above-mentioned Lobelia chinensis is referred to as Lobelia chinensis Lour., Banbyeonran or geubhaesaeg, is distributed in south central region and Cheju Island of Korea, and is inhabited in a gully, a stream, or a paddy field marsh. The Lobelia chinensis powder has traditionally had efficacies of diuresis, anti-inflammation, detoxification and others, and has been known to be used as a herbal medicine for treating asthma, dyspnea, pertussis, malignant tumor, eczema and traumatic-hemorrhagic.

The male cleanser may further include any one or more selected from the group consisting of perfume, a coloring agent, a preservative, an oxidation stabilizer, etc. within a range that does not inhibit effects of the composition in addition to the above-mentioned components.

Furthermore, a second aspect of the present invention provides a method of manufacturing a male cleanser, the method including the steps of: preparing a first mixture including purified water, glycerin, a first surfactant, hyaluronic acid, a viscosity increasing agent, arginine, a chelating agent, and a pH adjusting agent; mixing a second mixture including ethanol, 1,2-hexanediol, a second surfactant, menthol, perfume and chlorhexidine digluconate with the first mixture; and mixing a third mixture including purified water, a Morus alba root extract, a green tea extract, a persimmon leaf extract, an aloe vera leaf extract, a chamomile flower extract, a *Portulaca oleracea* L. extract and butylene glycol with the first mixture.

With regard to a method of manufacturing a male cleanser according to a second aspect of the present invention, detailed descriptions have been omitted with respect to parts of the second aspect overlapped with those of the first aspect of the present invention. However, contents of descriptions described in the first aspect of the present invention may be equally applied to the second aspect although the descriptions have been omitted in the second aspect.

According to an embodiment of the present invention, although the first surfactant may include purified water, sodium chloride and lauryl hydroxysultaine, and the second surfactant may include octyldodeceth-16, the present invention is not limited thereto.

FIG. 1 is a flowchart showing a method of manufacturing a male cleanser according to an embodiment of the present invention.

First, the method includes a step (S100) of preparing a first mixture.

According to an embodiment of the present invention, although the step of preparing the first mixture may be performed at a temperature of 50° C. to 70° C., the present invention is not limited thereto.

Subsequently, the method includes a step (S200) of mixing the second mixture with the first mixture.

According to an embodiment of the present invention, although the step of mixing the second mixture with the first mixture may further include a step of preparing the second mixture, the present invention is not limited thereto.

According to an embodiment of the present invention, although the step of preparing the second mixture may be performed at a temperature of 40° C. to 50° C., the present invention is not limited thereto.

According to an embodiment of the present invention, although the step of mixing the second mixture with the first mixture may include performing a stirring process at 1,500 rpm for 5 minutes, the present invention is not limited thereto.

Subsequently, the method includes a step (S300) of mixing the third mixture with the first mixture.

With regard to this, the first mixture to be mixed with the third mixture means that components of the second mixture are included in the first mixture.

According to an embodiment of the present invention, although the step of mixing the third mixture with the first mixture may further include a step of preparing the third mixture, the present invention is not limited thereto.

According to an embodiment of the present invention, although the step of preparing the third mixture may include the steps of: preparing a first material by mixing a Maca root extract, butylene glycol, purified water and 1,2-hexanediol; and preparing a second material by mixing purified water, butylene glycol, a Morus alba root extract, a green tea extract, a persimmon leaf extract and an aloe vera leaf extract, the present invention is not limited thereto.

According to an embodiment of the present invention, although the step of preparing the third mixture may be performed at a temperature of 40° C. to 50° C., the present invention is not limited thereto.

According to an embodiment of the present invention, although the step of mixing the third mixture with the first mixture may include performing a stirring process at 1,500 rpm for 3 minutes, the present invention is not limited thereto.

According to an embodiment of the present invention, although the method may include the steps of mixing the first mixture, the second mixture and the third mixture, cooling a resulting mixture at 30° C., and conducting a Q.C test, the present invention is not limited thereto.

Meanwhile, the method of manufacturing the male cleanser, without including the above-mentioned steps of the method, may include: a step (a) of mixing an emulsifier including 0.1 to 5 wt % of polyglyceryl-10 stearate, 0.1 to 5 wt % of polyglyceryl-3 methylglucose distearate and 0.1 to 5 wt % of polyglyceryl-3 diisostearate with oil including 0.1 to 5 wt % of isopropyl myristate, 0.1 to 5 wt % of macadamia oil, 0.1 to 5 wt % of silicone oil and 0.1 to 5 wt % of perfluoropolyether with respect to the total weight of a composition to obtain a mixture, and heating the mixture to a temperature of 75 to 85° C. to prepare an oil phase part;

a step (b) of mixing 5 to 20 wt % of a Maca extract, 10 to 30 wt % of a cleaning agent, 1 to 5 wt % of lauryl glucoside, 0.1 to 3 wt % of menthoxypropanediol, 0.01 to 0.5 wt % of a pH adjusting agent, 0.1 to 1 wt % of a disinfectant, 0.5 to 10 wt % of a block copolymer represented by the following chemical formula 1, and 30 to 70 wt % of water with respect to the total weight of the composition to obtain a mixture, and heating the mixture to a temperature of 75 to 85° C. to prepare a water phase part;

a step (c) of stirring the water phase part to 2,500 to 3,500 rpm within an emulsification tank, and injecting the oil phase part into the emulsification tank to stir the oil phase part to 2,500 to 3,500 rpm, thereby emulsifying the stirred materials to form a micro-sized first emulsion phase;

a cooling step (d) of cooling the first emulsion phase to a temperature of 37 to 50° C.; and a step (e) of injecting the first emulsion phase into a high pressure type emulsification machine at a temperature of 37 to 50° C. and secondly emulsifying the first emulsion phase to a pressure of 600 to 1,500 bars two to three times.

The method may include the step of additionally adding 3 to 10 wt % of a hot water extract of ingredients including 0.1 to 3 parts by weight of Mastic gum, and 0.1 to 3 parts by weight of a *Boswellia serrata* powder, 0.1 to 3 parts by weight of an erythritol powder, 0.1 to 3 parts by weight of a Sophora tonkinensis Gapnep powder and 0.1 to 3 parts by weight of a Lobelia chinensis powder to the water phase part of the step (b).

Hereinafter, the present invention will be described in more detail through Examples, but the Examples are only for the purpose of describing the present invention, and the scope of the present invention is not limited thereto.

Example 1

After mixing purified water, glycerin, sodium chloride, lauryl hydroxysultaine, decyl glucoside, xanthan gum, hyaluronic acid, arginine, hydroxyethyl cellulose, disodium EDTA, and citric acid to obtain a mixture, a first mixture was prepared by increasing temperature of the mixture to 50 to 60° C.

A second mixture was prepared by uniformly mixing ethanol, 1,2-hexanediol, menthol, octyldodeceth-16, chlorhexidine digluconate, and perfume at 40 to 45° C. Subsequently, after injecting the second mixture into the first mixture, the first and second mixtures were stirred to 1,500 rpm for 5 minutes to obtain a material having the first and second mixtures mixed therein.

After preparing a first material by mixing a Maca root extract, butylene glycol, purified water and 1,2-hexanediol, preparing a second material by mixing purified water, butylene glycol, a Morus alba root extract, a green tea extract, a persimmon leaf extract and an aloe vera leaf extract, uniformly mixing the first material, the second material, a

*Portulaca oleracea* L. extract, and a chamomile flower extract at 40 to 45° C. to obtain a mixture, injecting the mixture into the material having the first and second mixtures mixed therein, and stirring the mixture injected into the material having the first and second mixtures mixed therein to 1,500 rpm for 3 minutes, a resulting material was cooled to 30° C.

Example 2

After putting 1 kg of a Maca powder and 4 L of water into a heating container, boiling the Maca powder and water to 100° C. for 2 hours, and filtering the Maca powder through a filter paper to obtain a Maca powder-filtered solution, a Maca extract was prepared by boiling and concentrating the Maca powder-filtered solution until 1 L of an extracted solution was obtained.

Subsequently, after putting 300 g of Mastic gum, 300 g of a *Boswellia serrata* powder, 200 g of an erythritol powder, 100 g of a Sophora tonkinensis Gapnep powder, 100 g of a Lobelia chinensis powder, and 4 L of water into the heating container, boiling the Mastic gum, powders and water to 100° C. for 2 hours, and filtering the powders through a filter paper to obtain a powder-filtered solution, a mixed ingredient extract was prepared by boiling and concentrating the powder-filtered solution until 1 L of an extracted solution was obtained.

In order to produce polyacrylic acid substituted with a diisocyanate compound, 40 parts by weight of acrylic acid was injected into an 1 L reactor having a cooling device installed therein such that nitrogen gas is refluxed, and temperature is easily controlled. After injecting 60 parts by weight of ethyl acetate (EAc) as a solvent into the reactor, a purging process was performed using the nitrogen gas for 30 minutes. After maintaining temperature of the reactor to 60° C. and injecting 0.1 part by weight of azobisisobutyronitrile (AIBN), i.e., a reaction initiator into the reactor, an acrylic acid polymer with a weight average molecular weight of 1,500 was manufactured by reacting the acrylic acid, EAc and AIBN for 3 hours.

After injecting 100 parts by weight of ethyl acetate (EAc) as a solvent into an 1 L reactor having a cooling device installed therein such that nitrogen gas is refluxed, and temperature is easily controlled, 100 parts by weight of a solid of the above-manufactured acrylic acid polymer, 10 parts by weight of hexamethylene diisocyanate, 54 mg of magnesium trifluorosulfonate, 0.5 part by weight of Ionol and 0.15 part by weight of Tinuvin were injected into the reactor. The materials injected into the reactor were heated to 110° C. by performing a heating process. Acrylic acid substituted with hexamethylene diisocyanate was manufactured by performing the heating process for 15 hours.

In order to manufacture a block copolymer of poly(D,L-lactide-co-glycolide) and polyacrylic acid substituted with a diisocyanate compound, after injecting 100 ml of dimethylformamide and 290 mg of N,N-carbonyldiimidazole (CDI) into a reaction container, dimethylformamide and CDI were stirred in the reaction container. A solution was prepared by adding 20 g of poly(D,L-lactide-co-glycolide) with a number average molecular weight of 11,000 (RG502, Boehringer Ingelheim, Germany) to a mixture of dimethylformamide and CDI, thereby activating a hydroxy end group of poly(D,L-lactide-co-glycolide). After adding 0.5 mg of Ionol, 0.15 mg of Tinuvin and 25 g of the above-manufactured polyacrylic acid with a number average molecular weight of 2,000 to the solution, the Ionol, Tinuvin and polyacrylic acid added to the solution were heated to 110° C. After performing a heating process for 15 hours, filtering the heated material with a nylon filter with a pore size of 0.45 micrometer, and dispersing the filtered material in deionized water, a block copolymer with a weight average molecular weight of 54,000 was manufactured by removing unreacted materials and a reaction reagent through dialysis.

Subsequently, in order to prepare an oil-in-water type nanoemulsion male cleanser composition, an emulsifier including 3 wt % of polyglyceryl-10 stearate, 3 wt % of polyglyceryl-3 methylglucose distearate and 3 wt % of polyglyceryl-3 diisostearate with oil including 3 wt % of isopropyl myristate, 3 wt % of macadamia oil, 3 wt % of silicone oil and 3 wt % of perfluoropolyether with respect to the total weight of the composition to obtain a mixture, and the mixture was heated to a temperature of 75 to 85° C. to prepare an oil phase part.

10 wt % of a Maca extract, 20 wt % of sodium lauryl sulfate as a cleaning agent, 2 wt % of lauryl glucoside, 2 wt % of menthoxypropanediol, 0.3 wt % of citric acid, 0.5 wt % of ethanol as a disinfectant, 5 wt % of the block copolymer of poly(D,L-lactide-co-glycolide) and polyacrylic acid substituted with the diisocyanate compound, and 39.2 wt % of water with respect to the total weight of the composition to obtain a mixture, and the mixture was heated to a temperature of 75 to 85° C. to prepare a water phase part.

After stirring the water phase part to 2,500 to 3,500 rpm within an emulsification tank, injecting the oil phase part into the emulsification tank to stir the oil phase part to 2,500 to 3,500 rpm, and emulsifying the stirred materials, a micro-sized first emulsion phase was formed. The first emulsion phase was cooled to a temperature of 37 to 50° C. After injecting the first emulsion phase into a high pressure type emulsification machine at a temperature of 37 to 50° C., the male cleanser composition was prepared by secondly emulsifying the first emulsion phase to a pressure of 600 to 1,500 bars two to three times.

Example 3

A male cleanser composition was prepared by the same processes as in Example 2 except that 5 wt % of the mixed ingredient extract was additionally added to the water phase part.

Experimental Example 1

An experiment was conducted by allowing 200 adult men aged 25 to 55 to apply a male cleanser according to Example 1 of the present invention to their sexual organs. The experiment was progressed for total 7 weeks, and results were obtained by conducting interviews with subjects on a weekly basis during the experiment period.

TABLE 1

| Week | First question | Second question | Third question |
| --- | --- | --- | --- |
| First week | Δ | Δ | Δ |
| Second week | Δ | × | × |
| Third week | Δ | Δ | × |
| Fourth week | ○ | ○ | Δ |
| Fifth week | ○ | ○ | ○ |
| Sixth week | ○ | ○ | ○ |
| Seventh week | ○ | ○ | ○ |

With regard to this, the first question means if there is a change in length of his sexual organ by his own feeling, the second question means if he himself can visually confirm a change in length of his sexual organ, and the third question means if others can also feel a change in length of his sexual organ. Further, with regard to the first to third questions, ○ means exist, Δ means uncertain, and x means none.

Results of Table 1 were drawn up based on contents responded by 70% or more of the subjects. Referring to Table 1, when applying the male cleanser according to Example 1 to men's sexual organs, it can be confirmed that lengths of the sexual organs are extended after 5 weeks.

Experimental Example 2

Particle sizes of an emulsion of the male cleanser according to Example 2 were measured, and nano-emulsion stability was evaluated by a change in the particle sizes.

After respectively measuring particle sizes of water-in-oil type nanoparticle emulsion cosmetic compositions according to the present invention obtained in Example 2 by Mastersizer 2000 (Malvern Instrument, UK) using dynamic light scattering principle, measurement results are listed in the following Table 2. At this time, a process of measuring the particle sizes was performed under the following conditions after diluting the water-in-oil type nanoparticle emulsion cosmetic compositions with purified water such that turbidity values of nanoparticle emulsion-diluted solutions became 10 to 20%.

Measurement time: 2 minutes, the number of measurements per second: $5 \times 10^3$, temperature: 20° C., viscosity: 0.89 centipoise, particle refractive index: 1.4, dispersion medium refractive index: 1.33

After performing a process of measuring particle sizes twice, i.e., one day after preparation of the compositions and after storing the compositions at 40° C. for 6 months, and evaluating thermodynamic stability values of nanoemulsions after storing the compositions at high temperatures for a long period of time, measurement and evaluation results are listed in the following Table 2.

Experimental Example 3

Emulsification Stability Observed by the Naked Eye

After performing a process of evaluating the emulsification stability values by visually observing emulsification stability values of the compositions as follows along with a process of measuring particles sizes of the water-in-oil type nanoparticle emulsion cosmetic compositions obtained in Example 2, measurement and evaluation results are listed in the following Table 2.

Emulsification states of the compositions of Example 2 at room temperature (about 25° C.) right after the preparation and those after storage at 40° C. for 6 months were comparative observed. Unstable states including portions having sedimentation, separation, drainage, creaming, union or the like occurred therein were observed with the naked eye. Emusification stability is evaluated by percentage (%) of a stable portion except for an unstable portion from the whole portion, and is shown in the following equation.

Emulsification stability (%)=[(the whole portion−unstable portion)/the whole portion]×100%

TABLE 2

| Nano-particle emulsion cosmetic composition | Particle size (nm) | | Increase in particle sizes (%) | Emulsification stability observed by the naked eye (%) |
|---|---|---|---|---|
| | After storing at room temperature for one day since preparation | After storing at 40° C. for 6 months since preparation | | |
| Example 2 | 93 | 98 | 5.4 | 92 |

Experimental Example 4

Evaluating Performances of Male Cleanser Compositions

Performances for the male cleanser compositions of Examples 2 and 3 and performance for a male cleanser composition (product name: Rosemary power homme cleanser for men, manufacturer: C&I Cosmetics Co., Ltd.) of Comparative Example 1 were evaluated.

The experiment was conducted in such a manner that the men were allowed to give 1 to 10 points with respect to usability, incense, functionality after selecting 20 men in their 30s as experience groups, thereby allowing each of 10 of the men to use the male cleanser compositions of Example 2 and Comparative Example 1 once a day for 1 month and allowing the rest 10 men to use the male cleanser compositions of Example 3 and Comparative Example 1 once a day for 1 month.

The experience groups were allowed to evaluate functionality values by measuring positive feelings felt in sexual organ regions after using the male cleansers as scores.

After averaging the functionality values given by each of the experience groups to obtain an average functionality value, the average functionality value is listed in the following Table 3.

TABLE 3

| | Comparative Example 1 | Example 2 | Example 3 |
|---|---|---|---|
| Usability | 9.3 | 9.2 | 9.4 |
| Incense | 8.9 | 8.2 | 8.5 |
| Functionality | 2.3 | 8.5 | 8.4 |
| Total | 6.8 | 8.6 | 8.8 |

As confirmed from Table 3, the male cleansers of Examples 2 and 3 show performance values in usability and incense similar to those for the male cleanser of Comparative Example 1 on the market. However, the male cleansers of Examples 2 and 3 show remarkable effects in functionality performance values. As results of conducting interviews with users with regard to such differences, it was confirmed that the functionality performance values are results of evaluating feelings that sexual mainly functions were strengthened.

Although the exemplary embodiments of the present invention have been described in detail with reference to the accompanying drawings, the present invention is not limited thereto and may be embodied in many different forms without departing from the technical concept of the present invention. Therefore, the exemplary embodiments of the present invention are provided for illustrative purposes only but not intended to limit the technical spirit of the present invention. The scope of the technical spirit of the present invention is not limited thereto. Therefore, it should be understood that the above-described exemplary embodiments are illustrative in all aspects and do not limit the present invention.

The protective scope of the present invention should be construed based on the following claims, and all the technical concepts in the equivalent scope thereof should be construed as falling within the scope of the present invention.

The invention claimed is:

1. A male cleanser comprising: a skin conditioner, a solvent, a humectant, a viscosity increasing agent, a surfactant, a pH adjusting agent, a chelating agent, and perfume, wherein the skin conditioner includes a Maca root extract, a natural extract, chlorhexidine digluconate, arginine, menthol, and hyaluronic acid,
wherein the male cleanser comprises: 0.5 to 11 parts by weight of the Maca root extract and 0.1 to 5 parts by weight of the natural extract based on 100 parts by weight of the male cleanser.

2. The male cleanser of claim 1, wherein the natural extract includes a material selected from the group consisting of a Moms alba root extract, a green tea extract, a persimmon leaf extract, an aloe vera leaf extract, a chamomile flower extract, a *Portulaca oleracea* L. extract, and combinations thereof.

3. The male cleanser of claim 1, wherein the skin conditioner additionally includes a material selected from the group consisting of butylene glycol, purified water, 1,2-hexanediol, glycerin, and combinations thereof.

4. The male cleanser of claim 1, wherein the Maca root extract includes a material selected from the group consisting of a Maca powder, a Maca hot water extract, and a combination thereof.

5. The male cleanser of claim 1, wherein the solvent includes purified water, ethanol, glycerin, 1,2-hexanediol, and butylene glycol.

6. The male cleanser of claim 1, wherein the humectant includes glycerin.

7. The male cleanser of claim 1, wherein the male cleanser further comprises a viscosity increasing agent including a material selected from the group consisting of a xanthan gum, hydroxyethyl cellulose and a combination thereof, and a surfactant including cocamidopropyl betaine, sodium chloride, lauryl hydroxysultaine, decyl glucoside, and octyldodeceth-16.

8. The male cleanser of claim 1, wherein the male cleanser further comprises a chelating agent including citric acid and disodium EDTA.

9. The male cleanser of claim 1, wherein the male cleanser comprises 0.1 part by weight or less of chlorhexidine digluconate based on 100 parts by weight of the male cleanser.

10. The male cleanser of claim 1, wherein the male cleanser further includes a pH adjusting agent including citric acid.

11. A method of manufacturing a male cleanser, the method comprising the steps of:
preparing a first mixture including purified water, glycerin, a first surfactant, hyaluronic acid, a viscosity increasing agent, arginine, a chelating agent, and a pH adjusting agent;
mixing a second mixture including ethanol, 1,2-hexanediol, a second surfactant, menthol, perfume and chlorhexidine digluconate with the first mixture; and
mixing a third mixture including purified water, a Moms alba root extract, a green tea extract, a persimmon leaf extract, an aloe vera leaf extract, a chamomile flower extract, a *Portulaca oleracea* L. extract and butylene glycol with the first mixture.

12. The method of claim 11, wherein the first surfactant includes purified water, sodium chloride and lauryl hydroxysultaine, and the second surfactant includes octyldodeceth-16.

13. The method of claim 11, wherein the step of preparing the first mixture is performed at a temperature of 50° C. to 70° C.

14. The method of claim 11, wherein the step of preparing the third mixture includes the steps of:
preparing a first material by mixing a Maca root extract, butylene glycol, purified water and 1,2-hexanediol; and
preparing a second material by mixing purified water, butylene glycol, a Moms alba root extract, a green tea extract, a persimmon leaf extract and an aloe vera leaf extract.

* * * * *